United States Patent
Italiaie et al.

(10) Patent No.: US 11,432,848 B1
(45) Date of Patent: Sep. 6, 2022

(54) TOP LOADING QUICK LOCK CONSTRUCT

(71) Applicant: Warsaw Orthopedic, Inc., Warsaw, IN (US)

(72) Inventors: Christel Italiaie, Memphis, TN (US); William A. Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/318,279

(22) Filed: May 12, 2021

(51) Int. Cl.
*A61B 17/70* (2006.01)
*A61B 17/86* (2006.01)
*A61B 17/56* (2006.01)

(52) U.S. Cl.
CPC ...... *A61B 17/7032* (2013.01); *A61B 17/8605* (2013.01); *A61B 17/8685* (2013.01); *A61B 2017/564* (2013.01)

(58) Field of Classification Search
CPC ............ A61B 17/7032; A61B 17/8605; A61B 17/8685; A61B 2017/564
USPC ....... 606/264–270, 272, 278, 279, 305, 308, 606/328
See application file for complete search history.

(56) References Cited

U.S. PATENT DOCUMENTS

| | | |
|---|---|---|
| 3,604,487 A | 9/1971 | Gilbert |
| 3,844,291 A | 10/1974 | Moen |
| 4,411,259 A | 10/1983 | Drummond |
| 5,020,519 A | 6/1991 | Hayes et al. |
| 5,113,685 A | 5/1992 | Asher et al. |
| 5,207,678 A | 5/1993 | Harms et al. |
| 5,314,431 A | 5/1994 | Graziano |
| 5,330,472 A | 7/1994 | Metz-Stavenhagen |
| 5,364,397 A | 11/1994 | Hayes et al. |
| 5,389,099 A | 2/1995 | Hartmeister et al. |
| 5,449,361 A | 9/1995 | Preissman |
| 5,458,608 A | 10/1995 | Wortrich |
| 5,466,243 A | 11/1995 | Schmieding et al. |
| 5,575,792 A | 11/1996 | Errico et al. |
| 5,609,593 A | 3/1997 | Errico et al. |
| 5,609,654 A | 3/1997 | Le et al. |
| 5,616,143 A | 4/1997 | Schlapfer et al. |
| 5,630,817 A | 5/1997 | Rokegem et al. |

(Continued)

*Primary Examiner* — Eduardo C Robert
*Assistant Examiner* — David C Comstock
(74) *Attorney, Agent, or Firm* — Fox Rothschild LLP; P. Marshall Ticer

(57) ABSTRACT

Disclosed spinal implants may include a rod extending in a horizontal direction and a first implant receiver having a first passageway extending in the horizontal direction and a first threaded passageway extending in a vertical direction, for example. Additionally, the implant may include a second implant receiver having a second passageway extending in the horizontal direction and a second threaded passageway extending in the vertical direction, for example. The implant may include a first set screw having a size and shape corresponding to a size and shape of the first threaded passageway and a second set screw having a size and shape corresponding to a size and shape of the second threaded passageway, for example. In some embodiments, the rod may extend in the horizontal direction through the first and second passageways and may be constrained from moving in the vertical direction by the first and second passageways, for example.

19 Claims, 11 Drawing Sheets

(56) References Cited

U.S. PATENT DOCUMENTS

| | | |
|---|---|---|
| 5,643,263 A | 7/1997 | Simonson |
| 5,683,391 A | 11/1997 | Boyd |
| 5,720,751 A | 2/1998 | Jackson |
| 5,782,830 A | 7/1998 | Farris |
| 5,797,911 A | 8/1998 | Sherman et al. |
| 5,885,285 A | 3/1999 | Simonson |
| 5,899,901 A | 5/1999 | Middleton |
| 5,910,141 A | 6/1999 | Morrison et al. |
| 5,944,720 A | 8/1999 | Lipton |
| 5,947,967 A | 9/1999 | Barker |
| 6,036,692 A | 3/2000 | Burel et al. |
| 6,042,582 A | 3/2000 | Ray |
| 6,063,088 A | 5/2000 | Winslow |
| 6,074,391 A | 6/2000 | Metz-Stavenhagen et al. |
| 6,110,172 A * | 8/2000 | Jackson ............. A61B 17/7032 606/305 |
| 6,224,596 B1 * | 5/2001 | Jackson ............. A61B 17/7032 411/5 |
| 6,280,442 B1 | 8/2001 | Barker et al. |
| 6,415,693 B1 | 7/2002 | Simon et al. |
| 6,440,133 B1 | 8/2002 | Beale et al. |
| 6,497,166 B1 | 12/2002 | Fleckenstein |
| 6,520,962 B1 | 2/2003 | Taylor et al. |
| 6,562,038 B1 | 5/2003 | Morrison |
| 6,572,618 B1 | 6/2003 | Morrison |
| 6,579,292 B2 | 6/2003 | Taylor |
| 6,648,887 B2 | 11/2003 | Ashman |
| 6,685,705 B1 | 2/2004 | Taylor |
| 6,755,830 B2 | 6/2004 | Minfelde et al. |
| 6,857,343 B1 | 2/2005 | Easterbrooks et al. |
| 6,872,209 B2 | 3/2005 | Morrison |
| 6,945,933 B2 | 9/2005 | Branch et al. |
| 7,066,939 B2 | 6/2006 | Taylor |
| 7,226,453 B2 | 6/2007 | Chao et al. |
| 7,572,264 B2 | 8/2009 | Null et al. |
| 7,771,459 B2 | 8/2010 | von Oepen |
| 7,846,167 B2 | 12/2010 | Garcia et al. |
| 7,947,047 B2 | 5/2011 | Amal |
| 7,976,463 B2 | 7/2011 | Dewey et al. |
| 7,988,699 B2 | 8/2011 | Martz et al. |
| 8,048,124 B2 | 11/2011 | Chin et al. |
| 8,100,916 B2 | 1/2012 | Kumar et al. |
| 8,221,431 B2 | 7/2012 | Chenaux |
| 8,231,635 B2 | 7/2012 | Sharifi-Mehr et al. |
| 8,262,670 B2 | 9/2012 | Laubert et al. |
| 8,343,165 B2 | 1/2013 | Berrevoets |
| 8,394,108 B2 | 3/2013 | McLean et al. |
| 8,459,155 B2 | 6/2013 | Canizares, Jr. et al. |
| 8,460,307 B2 | 6/2013 | Saidha et al. |
| 8,475,466 B2 | 7/2013 | Chenaux |
| 8,540,756 B2 | 9/2013 | Olsen et al. |
| 8,585,741 B2 | 11/2013 | Gabelberger et al. |
| 8,747,411 B2 | 6/2014 | Mitchell |
| 8,757,035 B2 | 6/2014 | Kerboul et al. |
| 8,763,499 B2 | 7/2014 | Dahners |
| 8,784,431 B1 | 7/2014 | Harder et al. |
| 8,806,973 B2 | 8/2014 | Ross et al. |
| 8,845,652 B2 | 9/2014 | Heinz |
| 8,882,775 B2 | 11/2014 | LaPosta et al. |
| 8,900,248 B2 | 12/2014 | Biyani |
| 8,900,280 B2 | 12/2014 | Paroth et al. |
| 8,932,303 B2 | 1/2015 | Bouliane |
| 8,945,193 B2 | 2/2015 | Kirschman |
| 8,951,264 B2 | 2/2015 | Saidha et al. |
| 8,968,276 B2 | 3/2015 | Zemlok et al. |
| 8,986,349 B1 * | 3/2015 | German ............. A61B 17/7068 606/279 |
| 8,992,575 B1 | 3/2015 | Di Lauro et al. |
| 8,992,587 B2 | 3/2015 | Kirschman |
| 8,998,921 B2 | 4/2015 | Sharifi-Mehr et al. |
| 9,017,333 B2 | 4/2015 | Beale et al. |
| 9,055,943 B2 | 6/2015 | Zemlok et al. |
| 9,089,371 B1 | 7/2015 | Faulhaber |
| 9,113,976 B2 | 8/2015 | Yevmenenko et al. |
| 9,138,279 B2 | 9/2015 | Laposta et al. |
| 9,149,307 B2 | 10/2015 | Sandstrom et al. |
| 9,216,044 B2 | 12/2015 | Nuckley et al. |
| 9,265,540 B2 | 2/2016 | Kirschman |
| 9,295,500 B2 | 3/2016 | Marigowda |
| 9,314,274 B2 | 4/2016 | Amstutz et al. |
| 9,387,025 B2 | 7/2016 | Santangelo et al. |
| 9,402,663 B2 | 8/2016 | Peterson et al. |
| 9,446,507 B2 | 9/2016 | Nino et al. |
| 9,526,553 B2 | 12/2016 | Bess et al. |
| 9,572,605 B2 | 2/2017 | Shipp |
| 9,597,135 B1 | 3/2017 | Miller et al. |
| 9,642,654 B2 | 5/2017 | Reimels et al. |
| 9,649,139 B2 | 5/2017 | Sharifi-Mehr et al. |
| 9,687,285 B2 | 6/2017 | Robinson |
| 9,724,149 B2 | 8/2017 | Trieu et al. |
| 9,808,354 B2 | 11/2017 | Willis et al. |
| 9,820,740 B2 | 11/2017 | Zemlok et al. |
| 9,855,087 B2 | 1/2018 | Divincenzo et al. |
| 9,949,731 B2 | 4/2018 | Erramilli et al. |
| 9,956,003 B2 | 5/2018 | Prevost |
| 9,968,384 B2 | 5/2018 | Fischer et al. |
| 9,987,066 B2 | 6/2018 | Stad et al. |
| 10,045,787 B2 | 8/2018 | Krebs et al. |
| 10,076,374 B2 | 9/2018 | Diduch et al. |
| 10,105,165 B2 | 10/2018 | Biedermann et al. |
| 10,117,684 B2 | 11/2018 | Saidha et al. |
| 10,160,105 B2 | 12/2018 | Nino et al. |
| 10,219,854 B2 | 3/2019 | Nino et al. |
| 10,274,021 B2 | 4/2019 | Victor et al. |
| 10,285,740 B2 | 5/2019 | May et al. |
| 10,349,986 B2 | 7/2019 | Wall et al. |
| 10,363,073 B2 | 7/2019 | Raina et al. |
| 10,390,967 B2 | 8/2019 | Livorsi et al. |
| 10,426,535 B2 | 10/2019 | Zander et al. |
| 10,433,883 B2 | 10/2019 | DiVincenzo et al. |
| 10,433,982 B2 | 10/2019 | Willis et al. |
| 10,448,978 B2 | 10/2019 | Wall et al. |
| 10,463,404 B2 | 11/2019 | Wall et al. |
| 10,470,805 B2 | 11/2019 | Biedermann et al. |
| 10,478,235 B2 | 11/2019 | Beale et al. |
| 10,568,668 B2 | 2/2020 | Biedermann et al. |
| 10,568,677 B2 | 2/2020 | DiVincenzo et al. |
| 10,582,925 B2 | 3/2020 | Marks et al. |
| 10,603,078 B2 | 3/2020 | Simpson et al. |
| 10,639,080 B2 | 5/2020 | Sharifi-Mehr et al. |
| 10,646,261 B2 | 5/2020 | Folger et al. |
| 10,653,457 B2 | 5/2020 | Erramilli et al. |
| 10,660,687 B2 | 5/2020 | Goodwin, Jr. et al. |
| 10,682,167 B2 | 6/2020 | Sandstrom et al. |
| 10,702,315 B2 | 7/2020 | Lindner |
| 10,702,316 B2 | 7/2020 | Heuer |
| 10,709,488 B2 | 7/2020 | Diduch et al. |
| 10,729,419 B2 | 8/2020 | Diduch et al. |
| 10,751,092 B2 | 8/2020 | Biedermann et al. |
| 10,765,466 B2 | 9/2020 | Stad et al. |
| 10,779,872 B2 | 9/2020 | Smith et al. |
| 10,869,751 B2 | 12/2020 | Diduch et al. |
| 10,874,448 B2 | 12/2020 | Rees et al. |
| 2002/0166421 A1 | 11/2002 | Bowerman |
| 2002/0169453 A1 | 11/2002 | Berger |
| 2005/0159750 A1 | 7/2005 | Doherty |
| 2005/0203519 A1 * | 9/2005 | Harms ............... A61B 17/7026 606/254 |
| 2005/0273101 A1 | 12/2005 | Schumacher |
| 2006/0041261 A1 | 2/2006 | Osypka |
| 2006/0052785 A1 * | 3/2006 | Augostino ......... A61B 17/7043 606/247 |
| 2006/0241593 A1 | 10/2006 | Sherman et al. |
| 2006/0241600 A1 | 10/2006 | Ensign et al. |
| 2007/0010816 A1 | 1/2007 | Wilkinson et al. |
| 2007/0122764 A1 | 5/2007 | Balfour et al. |
| 2008/0015596 A1 | 1/2008 | Whipple |
| 2008/0041196 A1 | 2/2008 | Companioni et al. |
| 2008/0071274 A1 | 3/2008 | Ensign |
| 2008/0147126 A1 | 6/2008 | Tipirneni et al. |
| 2008/0147128 A1 | 6/2008 | Fritzinger |
| 2008/0154373 A1 * | 6/2008 | Protopsaltis .......... A61F 2/4425 623/17.12 |
| 2008/0200918 A1 | 8/2008 | Spitler et al. |

(56) References Cited

U.S. PATENT DOCUMENTS

| | | |
|---|---|---|
| 2008/0215099 A1 | 9/2008 | Balfour et al. |
| 2008/0269768 A1 | 10/2008 | Schwager et al. |
| 2009/0005787 A1 | 1/2009 | Crall et al. |
| 2009/0264895 A1 | 10/2009 | Gasperut et al. |
| 2010/0010543 A1* | 1/2010 | Jackson ............... A61B 17/702 606/254 |
| 2010/0063546 A1* | 3/2010 | Miller ............... A61B 17/7038 606/278 |
| 2010/0249798 A1 | 9/2010 | Sournac et al. |
| 2010/0249846 A1 | 9/2010 | Simonson |
| 2011/0077693 A1 | 3/2011 | Yu |
| 2011/0137320 A1 | 6/2011 | von Oepen |
| 2011/0160775 A1 | 6/2011 | Carls et al. |
| 2011/0270321 A1 | 11/2011 | Prevost et al. |
| 2011/0270322 A1 | 11/2011 | Olsen et al. |
| 2011/0282398 A1 | 11/2011 | Overes et al. |
| 2011/0301650 A1 | 12/2011 | Johnson et al. |
| 2012/0046700 A1* | 2/2012 | Jackson ............. A61B 17/7037 606/305 |
| 2012/0123481 A1 | 5/2012 | Lin |
| 2012/0203288 A1 | 8/2012 | Lange et al. |
| 2012/0215263 A1 | 8/2012 | Lee |
| 2012/0239095 A1 | 9/2012 | Barrall |
| 2012/0253398 A1 | 10/2012 | Metcalf et al. |
| 2012/0277798 A1* | 11/2012 | Benson ............. A61B 17/7008 606/264 |
| 2013/0072984 A1 | 3/2013 | Robinson |
| 2013/0072986 A1 | 3/2013 | Robinson |
| 2013/0261671 A1 | 10/2013 | Horvath |
| 2014/0018816 A1 | 1/2014 | Fenn et al. |
| 2014/0066945 A1 | 3/2014 | Humphreys et al. |
| 2014/0142639 A1 | 5/2014 | Vennard et al. |
| 2014/0172027 A1 | 6/2014 | Biedermann et al. |
| 2014/0257411 A1 | 9/2014 | Rezach |
| 2014/0288567 A1 | 9/2014 | Kroll |
| 2014/0324062 A1 | 10/2014 | Heuer et al. |
| 2015/0039034 A1* | 2/2015 | Frankel ................ A61B 90/06 606/261 |
| 2015/0201972 A1 | 7/2015 | Doubler et al. |
| 2015/0201987 A1 | 7/2015 | Lemoine et al. |
| 2015/0250521 A1 | 9/2015 | Poker et al. |
| 2015/0359575 A1 | 12/2015 | Pech et al. |
| 2015/0374417 A1 | 12/2015 | Petit et al. |
| 2016/0278815 A1 | 9/2016 | Fitzpatrick |
| 2016/0317206 A1 | 11/2016 | Rezach et al. |
| 2017/0119537 A1 | 5/2017 | Tepper et al. |
| 2017/0245898 A1 | 8/2017 | May et al. |
| 2018/0049777 A1 | 2/2018 | Rezach |
| 2018/0070941 A1 | 3/2018 | Zemlok et al. |
| 2018/0071000 A1 | 3/2018 | Pham et al. |
| 2018/0110548 A1 | 4/2018 | May et al. |
| 2018/0146990 A1 | 5/2018 | Manzanares et al. |
| 2018/0153600 A1 | 6/2018 | Koller et al. |
| 2018/0193062 A1 | 7/2018 | May |
| 2018/0193063 A1 | 7/2018 | May |
| 2018/0206890 A1 | 7/2018 | Rezach |
| 2018/0235684 A1 | 8/2018 | Hawkes et al. |
| 2018/0353224 A1 | 12/2018 | Kam et al. |
| 2019/0076170 A1 | 3/2019 | Lehman, Jr. et al. |
| 2019/0159820 A1 | 5/2019 | Geist et al. |
| 2019/0175193 A1 | 6/2019 | Fenn et al. |
| 2019/0183535 A1* | 6/2019 | May ..................... A61B 17/702 |
| 2019/0254729 A1 | 8/2019 | Rohlfing et al. |
| 2019/0254730 A1 | 8/2019 | Rohlfing et al. |
| 2019/0329388 A1 | 10/2019 | Erickson et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030015 A1 | 1/2020 | Grizzard et al. |
| 2020/0038064 A1 | 2/2020 | Stoklund et al. |
| 2020/0078056 A1 | 3/2020 | Biedermann et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0121397 A1 | 4/2020 | Elliott et al. |
| 2020/0121398 A1 | 4/2020 | Elliott et al. |
| 2020/0205805 A1 | 7/2020 | Marks et al. |
| 2020/0229849 A1 | 7/2020 | Biedermann et al. |
| 2020/0237412 A1 | 7/2020 | Erramilli et al. |
| 2020/0340558 A1 | 10/2020 | Riemhofer et al. |
| 2020/0375638 A1 | 12/2020 | Avidano et al. |
| 2020/0390478 A1 | 12/2020 | Rodriguez et al. |
| 2020/0390486 A1 | 12/2020 | Rodriguez et al. |

* cited by examiner

TOP LOADING QUICK LOCK CONSTRUCT

CROSS-REFERENCE TO RELATED APPLICATIONS

This application incorporates by reference U.S. Pat. No. 10,335,201, titled Spinal Implant System and Methods of Use, filed Jan. 25, 2017; U.S. Pat. No. 10,653,455 titled Spinal Implant System and Methods of Use filed Sep. 12, 2017; U.S. Pat. No. 6,790,209, titled Rod Reducer Instruments and Methods, filed Jul. 1, 2002; U.S. application Ser. No. 17/167,258, titled Instrument for locking Orthopedic Screws, filed Feb. 4, 2021; and U.S. application Ser. No. 17/104,897, titled Combination Set Screw Breakoff and Tab Breaker Instrument, filed Feb. 3, 2021. The entire contents of each are incorporated herein by reference.

FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods, spinal constructs, and bone fasteners can be delivered to a surgical site. The rods may be independently attached via a spinal construct and/or a plurality of spinal constructs to the exterior of two or more vertebral members. This disclosure describes an improvement over these prior technologies.

SUMMARY

The techniques of this disclosure generally relate to top loading spinal constructs. In various embodiments, a top loading spinal construct may include two implant receivers that may support a rod and be connected to a pair of bone screws, respectively. Some embodiments may optionally be pre-assembled for rapid installation and/or ease of installation.

In one aspect, the present disclosure provides for an implant. The implant may include a rod extending in a lateral direction and a first implant receiver having a first passageway extending through a first sidewall and a second sidewall of the first implant receiver in a lateral direction, for example. In various embodiments, the first implant receiver may have a first threaded passageway extending in a longitudinal direction, for example Additionally, the implant may include a second implant receiver having a second passageway extending through a third sidewall and a fourth sidewall of the second implant receiver in the lateral direction, for example. Furthermore, the second implant receiver may have a second threaded passageway extending in the longitudinal direction, for example. In various embodiments, the implant may include a first set screw having a first outside thread pattern extending along an outside circumferential surface of the first set screw and having a size and shape corresponding to a size and shape of the first threaded passageway, for example. In various embodiments, the implant may include a second set screw having a second outside thread pattern extending along an outside circumferential surface of the second set screw and having a size and shape corresponding to a size and shape of the second threaded passageway, for example. In some embodiments, the rod may extend in the lateral direction through the first and second passageways and may be constrained from moving in the longitudinal direction by the first and second passageways, for example.

In another aspect, the disclosure provides for a method of installing a spinal implant. The method may include the step of providing a pre-assembled implant, that includes a rod extending in a lateral direction and a first implant receiver having a first passageway extending through a first sidewall and a second sidewall of the first implant receiver in the lateral direction, for example. In various embodiments, the first implant receiver may have a first threaded passageway extending in a longitudinal direction and a first base portion for coupling to a first bone screw, for example. In various embodiments, a second implant receiver may have a second passageway extending through a third sidewall and a fourth sidewall of the second implant receiver in the lateral direction, for example. In various embodiments, the second implant receiver may have a second threaded passageway extending in the longitudinal direction and a second base portion for coupling to a second bone screw, for example. In various embodiments, a first set screw having a first outside thread pattern extending along an outside circumferential surface of the first set screw and having a size and shape corresponding to a size and shape of the first threaded passageway may be provided. Additionally, in various embodiments, a second set screw having a second outside thread pattern extending along an outside circumferential surface of the second set screw and having a size and shape corresponding to a size and shape of the second threaded passageway may be provided. In some embodiments, the rod may extend in the lateral direction through the first and second passageways and may be constrained from moving in the longitudinal direction by the first and second passageways, for example. The method may further include the step of securing first and second bone screws to a patient and securing the pre-assembled spinal implant to the first and second bone screws, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
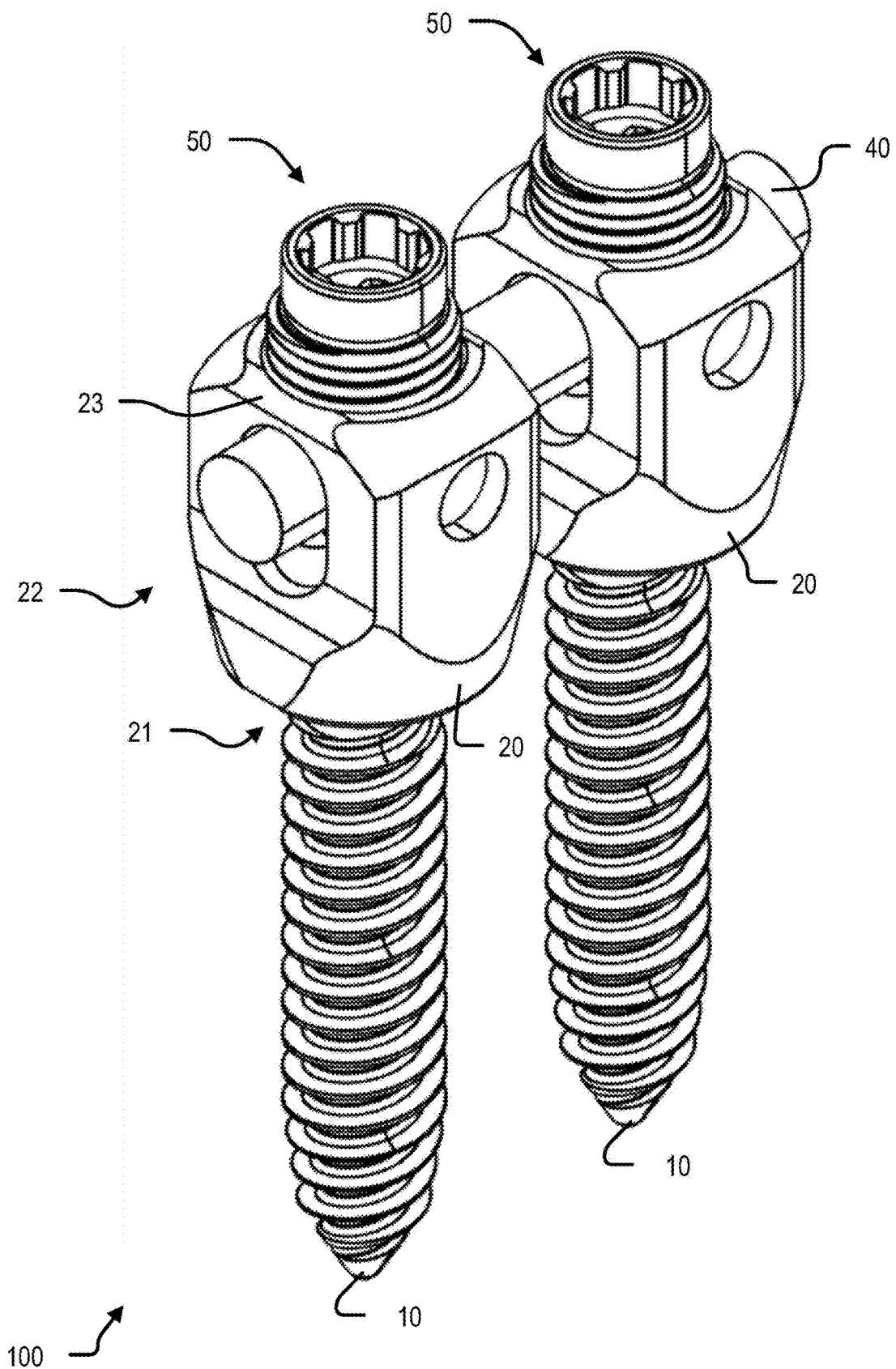
FIG. 1 is a perspective view of a spinal implant system.

Embodiments of the present disclosure relate generally, for example, to spinal stabilization systems, and more particularly, to top loading spinal constructs. In some embodiments, a top loading spinal construct may include two implant receivers that may support a rod and be connected to a pair of bone screws, respectively. In some embodiments, the two implant receivers and the rod may optionally be pre-assembled for rapid installation and/or ease of installation to the pair of bone screws. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-10 generally, various spinal implant systems 100 are disclosed. The components of spinal implant system 100 can be fabricated from biologically acceptable materials suitable for medical applications, including metals, synthetic polymers, ceramics and bone material and/or their composites. For example, the components of spinal implant system 100, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 100 may have material composites, including the above materials, to achieve various desired characteristics such as strength, rigidity, elasticity, compliance, biomechanical performance, durability and radiolucency or imaging preference. The components of spinal implant system 100, individually or collectively, may also be fabricated from a heterogeneous material such as a combination of two or more of the above-described materials, for example. The components of spinal implant system 100 may be monolithically formed, integrally connected or include fastening elements and/or instruments, as described herein.

Figure 2:
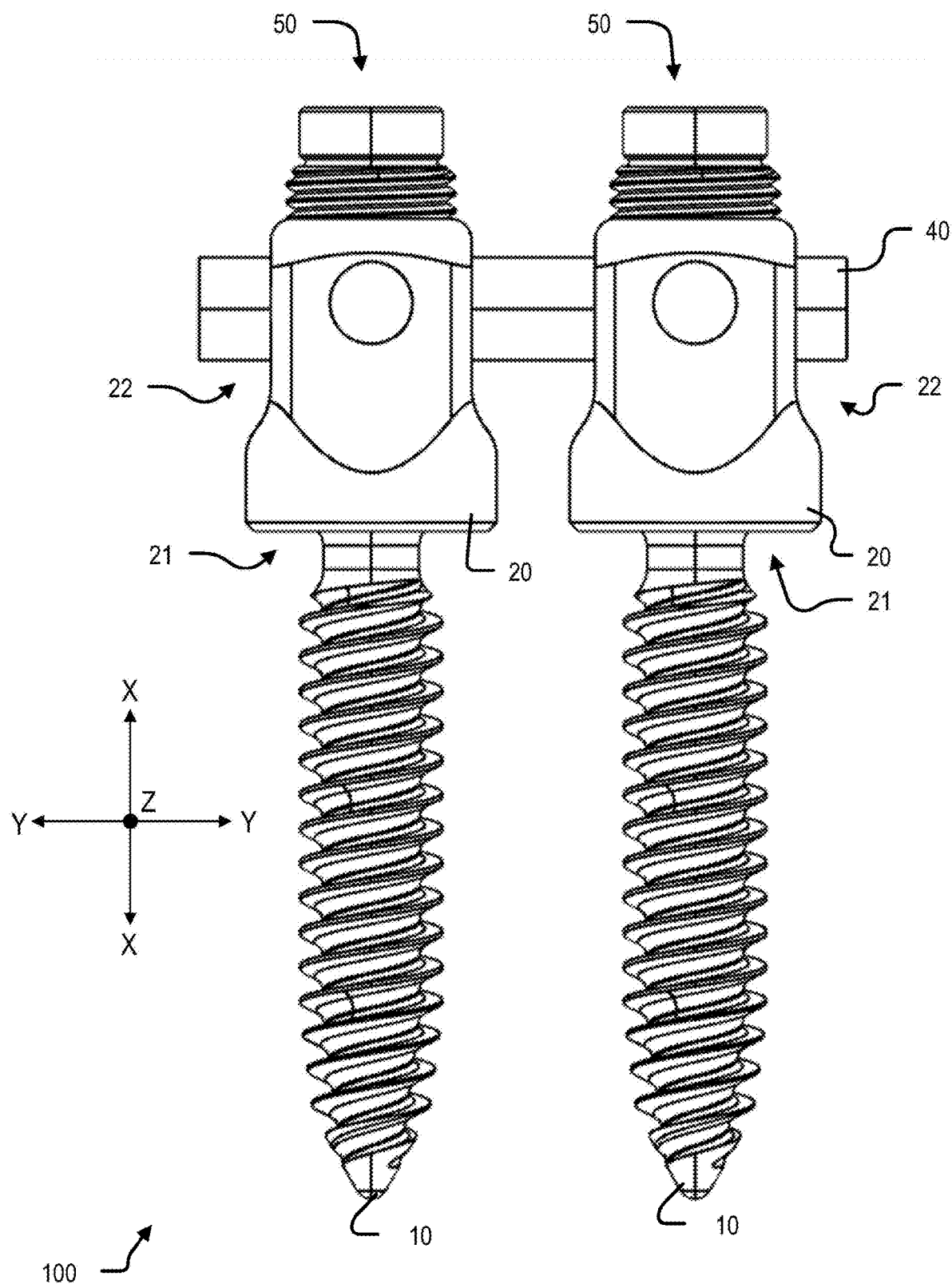
FIG. 2 is a side view of a spinal implant system.

FIG. 1 is a perspective view of a spinal implant system 100 and FIG. 2 is a side view of spinal implant system 100. Spinal implant system 100 may include a first implant receiver 20 and a second implant receiver 20. In the example embodiment, first and second implant receivers 20 are the same type of implant receiver. However, in other embodiments, first and second implant receivers 20 may be substantially the same, and or similar to one another. First and second implant receivers 20, may each include a passageway 22 for receiving a rod 40, for example. Additionally, first and second implant receivers 20 may include first and second set screws 50, respectively. Set screws 50 may move upward and downward in the vertical direction, labeled as X direction in FIG. 2, to secure rod 40 within passageway 22, for example. In various embodiments, set screw 50 may be a breakoff setscrew having a breakoff portion 52 (see FIG. 2), for example. In other embodiments, set screw 50 may be a solid setscrew without a breakoff portion, for example.

Figure 8:
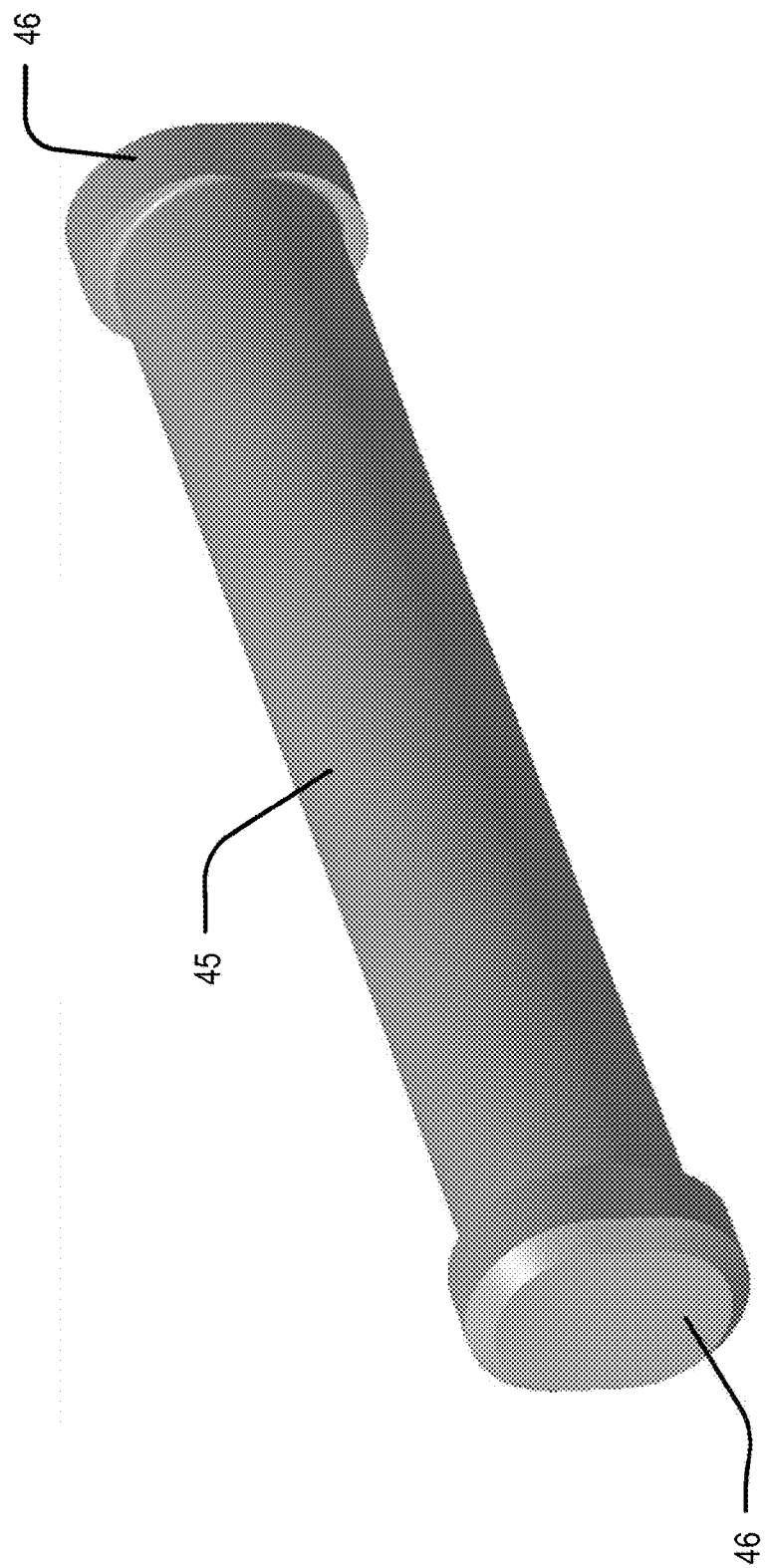
FIG. 8 is a perspective view of a rod for use with disclosed spinal implant systems.

In the example embodiment, each passageway 22 may comprise an aperture extending through the side of implant receiver 20. In the example embodiment, the passageway 22 is closed at the upper end 23 of implant receiver 20 such that the rod 40 is confined within the passageway 22 in two dimensions. In various embodiments, the solid upper end 23 is disposed above the passageway 22. For example, in various embodiments, the passageway 22 may confine the rod 40 in the vertical direction (labeled as X direction in FIG. 2), and in the lateral direction (labeled as Z direction in FIG. 2) but still permit some sliding in the horizontal direction (labeled as Y direction in FIG. 2). For example, a perimeter of the passageway 22 is enclosed in the vertical direction and in the lateral direction. For example, as illustrated in FIG. 2, the rod 40 is confined in the vertical direction and in the lateral direction by passageway 22 but may permit movement in the horizontal direction. However, as shown in FIG. 8, some embodiments may utilize an alternate rod 45 having closed end caps 46, which may constrain rod 45 from moving too far in the horizontal direction and sliding out of passageway 22, for example.

Figure 3B:
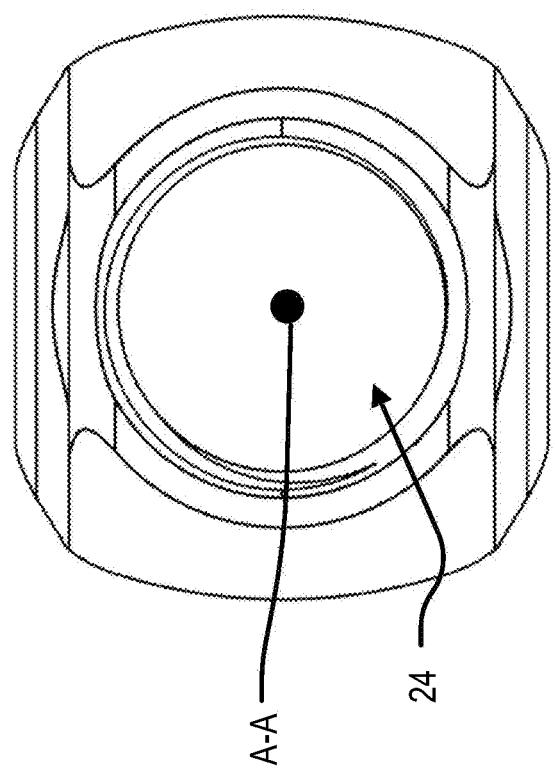
FIG. 3B is a top view of a receiver for use with disclosed spinal implant systems.
Figure 3A:
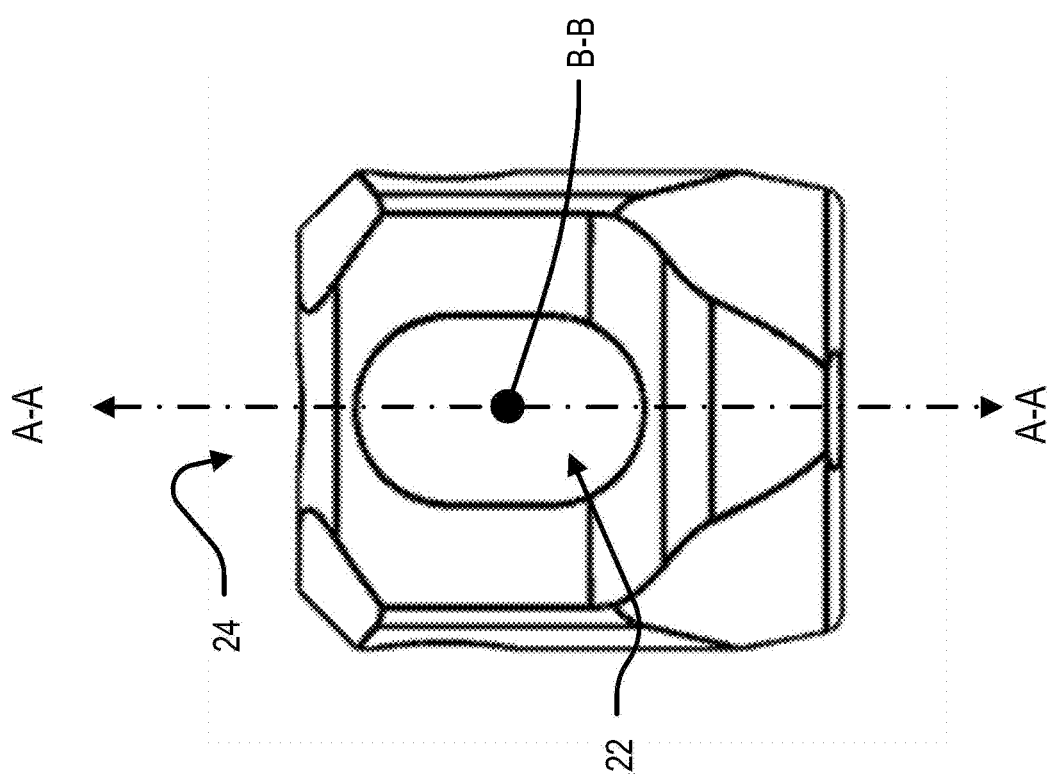
FIG. 3A is a side view of a receiver for use with disclosed spinal implant systems.

FIG. 3A is a side view of an implant receiver 20 and FIG. 3B is a top view of a receiver for use with disclosed spinal implant systems 100. In the example illustration, implant receiver 20 may include a threaded passageway 24 for rotatably supporting and receiving set screw 50, for example. Threaded passageway 24 may extend in the vertical direction and define a vertical axis A-A of which set screw 50 may move upward and downward in upon rotation of set screw 50. Additionally, implant receiver 20 may include a passageway 22 for receiving rod 40, for example. Passageway 22 may extend in the horizontal direction and define a horizontal axis B-B, which rod 40 may be coaxially aligned with, for example. In the example embodiment, passageway 22 may be shaped like an oval when viewed in a side perspective view as shown in FIG. 3A. In other embodiments, passageway 22 may be shaped like a circle, or a square, for example. In various embodiments, passageway 22 may have a size and shape generally corresponding to a size and shape of rod 40, for example. In various embodiments, a side view cross section of rod 40 may have an oval like shape generally corresponding to a size and shape of passageway 22, for example.

Figure 4:
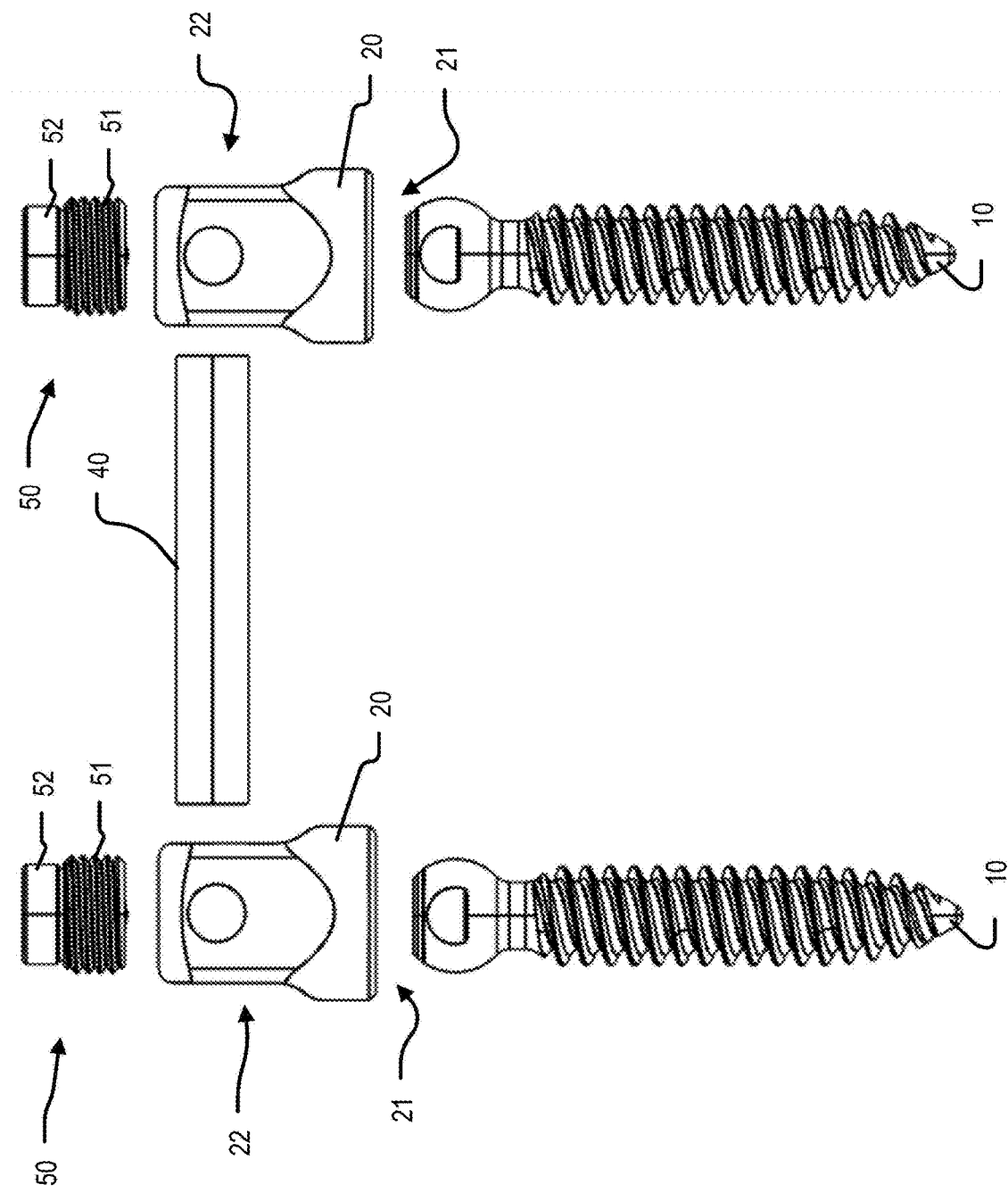
FIG. 4 is a side view exploded parts diagram of a spinal implant system.
Figure 5:
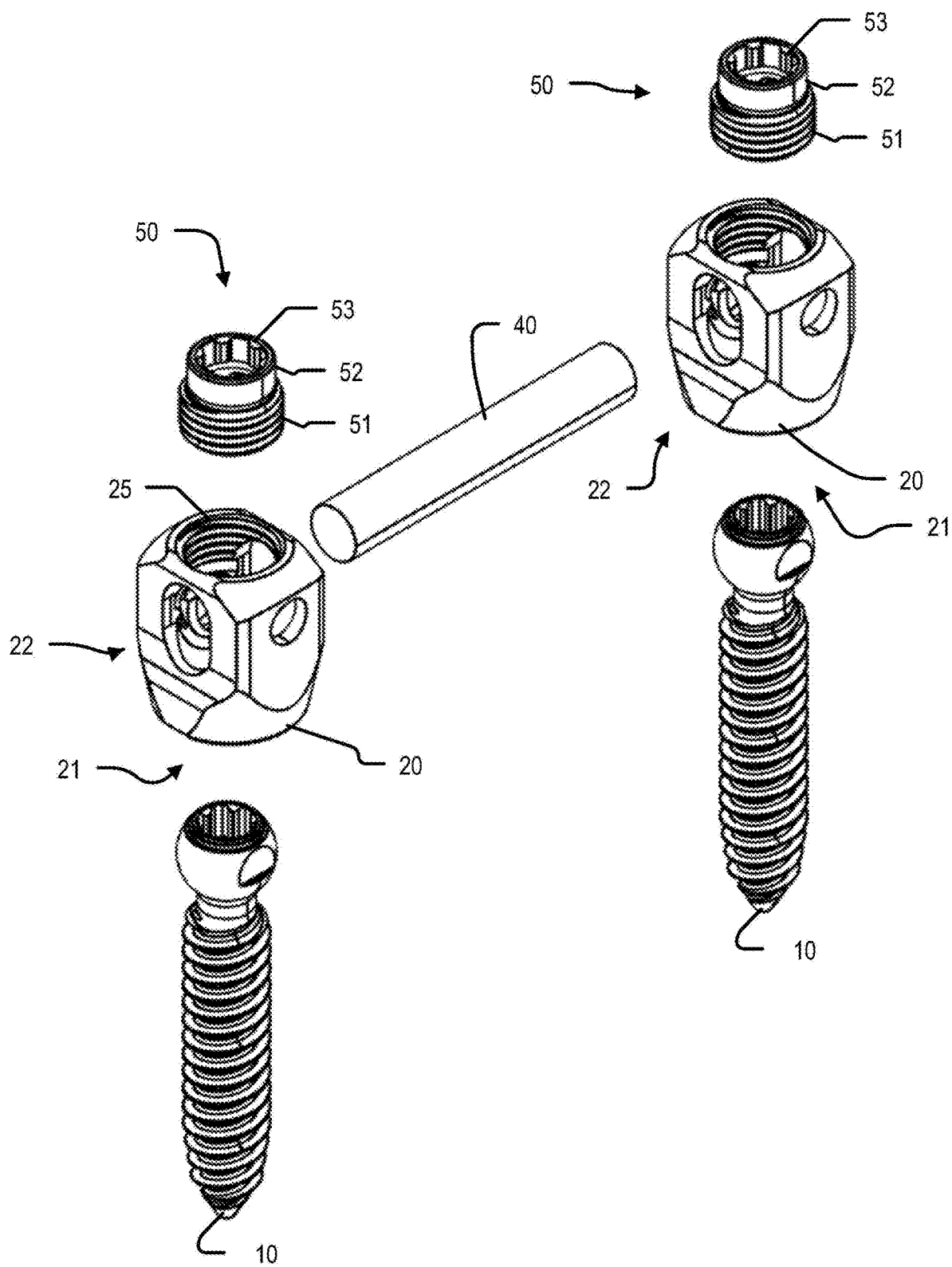
FIG. 5 is a perspective view exploded parts diagram of a spinal implant system.

FIG. 4 is a side view exploded parts diagram of a spinal implant system 100 and FIG. 5 is a perspective view exploded parts diagram of a spinal implant system 100. In the example illustrations, it is shown that set screw 50 may have an exterior thread pattern 51 having a timing and/or pitch including a size and shape generally corresponding to the timing and or pitch of threads 25 of threaded passageway 24 for example. Additionally, set screw 50 may include a drive end 53 for coupling to a driver (not illustrated) to rotate set screw 50, for example. Drive end 53 may take any shape, for example a hexalobular shape, a hexaganol shape, a torx shape, etc. In operation, an end user may secure rod 40 within passageway 22 of the first and second implant receivers 20 and securely tighten set screw 50 by rotating set screw 50 at drive end 53 such that set screw 50 advances downward along the vertical axis A-A and secures rod 40 against the lower walls of passageway 22, for example.

Figure 6:
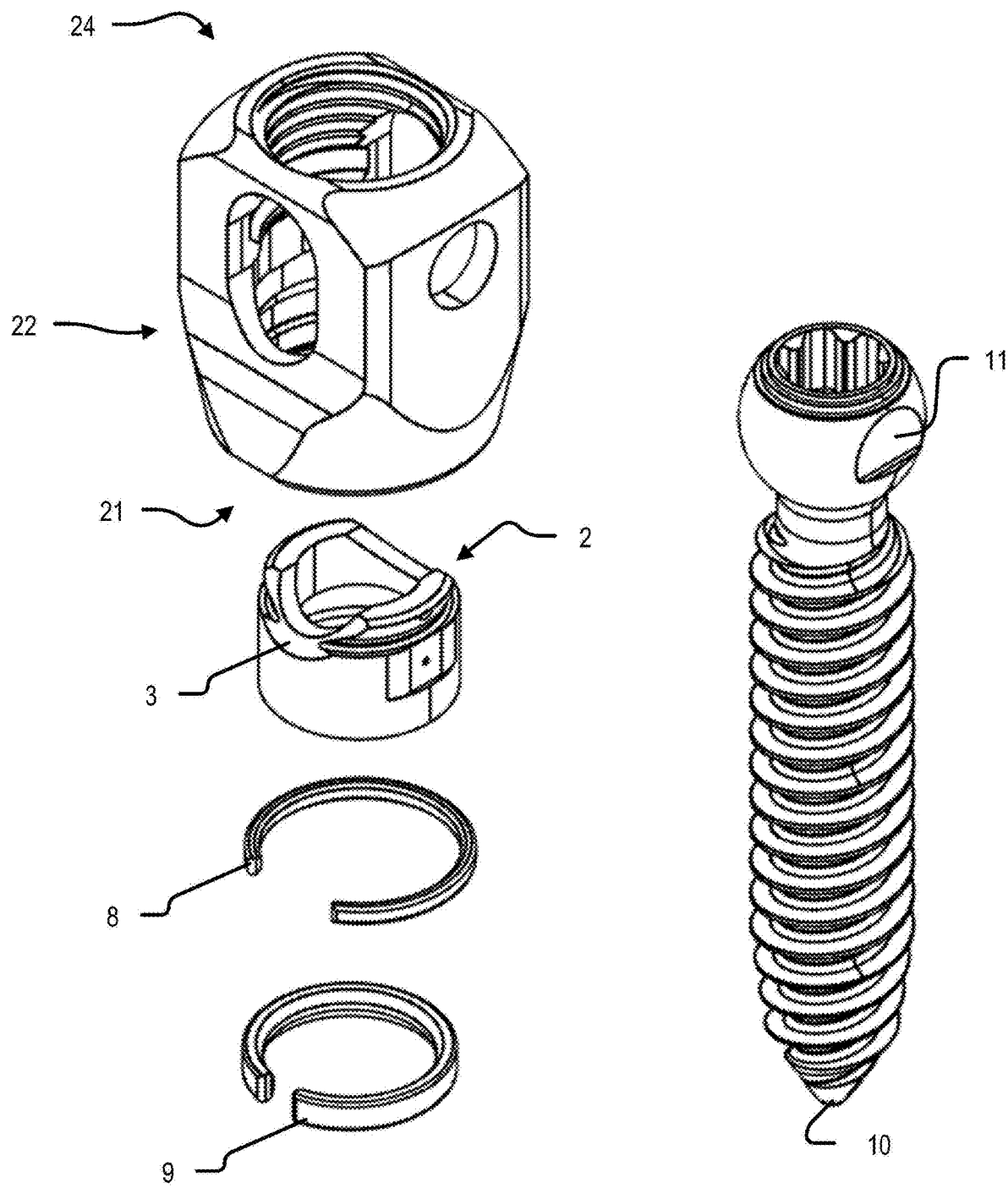
FIG. 6 is a perspective view exploded parts diagram of a receiver and various components for connecting to a bone screw.

FIG. 6 is a perspective view exploded parts diagram of an implant receiver 20 for use with disclosed spinal implant systems 100. In the example illustration, it is shown that implant receiver 20 may include a base portion 21 having a lower cavity configured to securely couple to bone screw 10 and support a crown 2 in a position above the head portion 11 of bone screw 10, for example. Crown 2 may include curved support surfaces 3 having a size and shape corresponding to a lower portion of the curved surface of rod 40, for example. Accordingly, crown 2 may support rod 40 from beneath rod 40 by directly contacting an underside of rod 40. Additionally, rod 40 may bear down on the lower surface of passageway 22. Spinal implant system 100 may further include an upper ring 8 and a lower ring 9. Upper and lower rings 8, 9 may be C-shaped and configured to securely couple head portion 11 of bone screw 10 within lower cavity of base portion 21, for example. Additional examples of how implant receiver 20 may securely connect to a bone screw 10 via an internal cavity of base portion 21 are also disclosed in detail in each of U.S. Pat. No. 10,335,201, titled Spinal Implant System and Methods of Use; and U.S. Pat. No. 10,653,455 titled Spinal Implant System and Methods of Use; U.S. application Ser. No. 17/167,258, titled Instrument for locking Orthopedic Screws, which are all incorporated herein by reference in their entireties.

Figure 7:
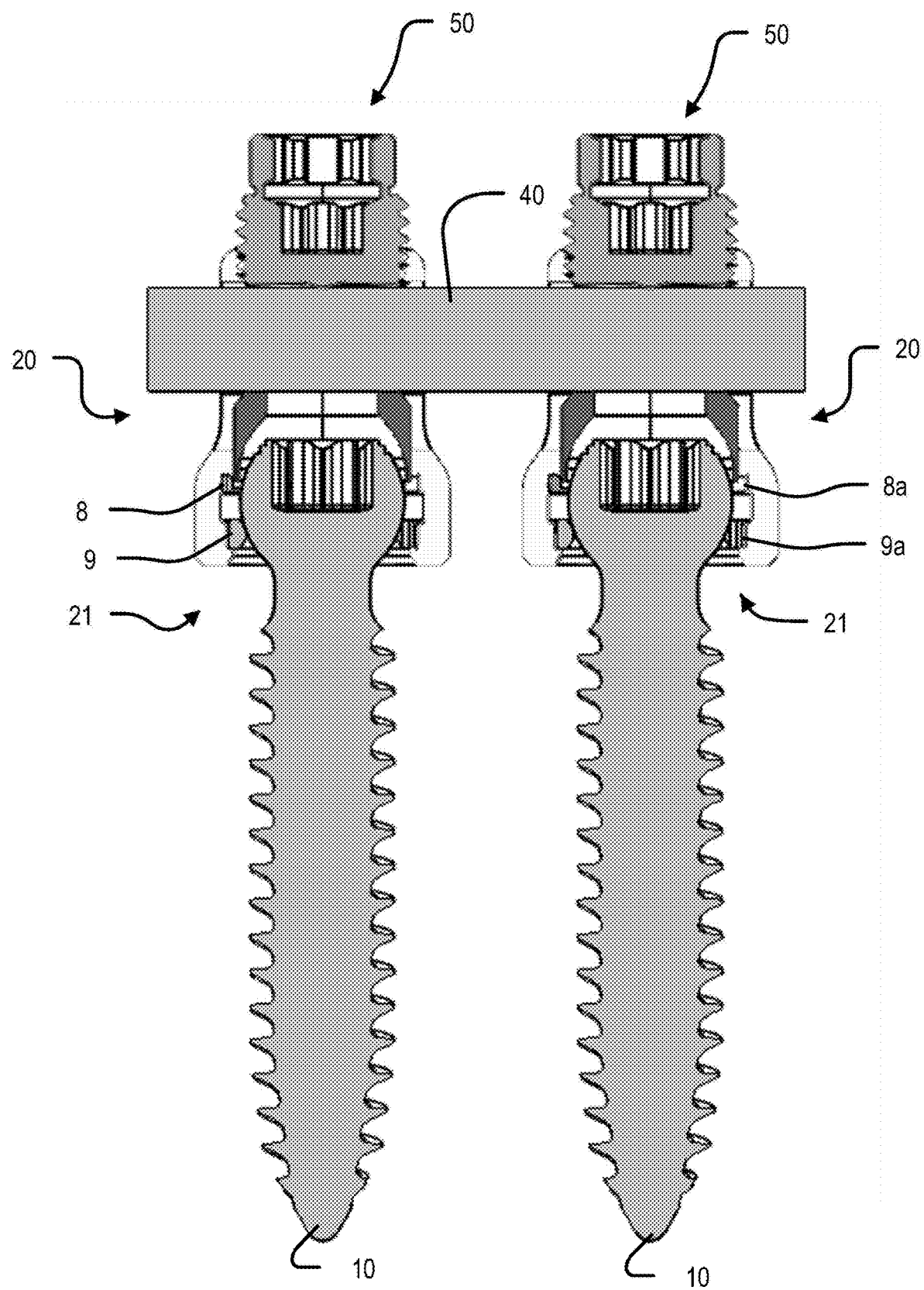
FIG. 7 is a side cross section view of a spinal implant system.

FIG. 7 is a side cross section view of spinal implant system 100. In the example illustration, the first and second implant receivers 20 are securely coupled to uniaxial bone screws 10. For example, a surgeon may initially couple the first and second implant receivers 20 to respective bone screws 10 by pushing each of implant receivers 20 down against the bone screw 10 by, e.g., an instrument for locking orthopedic screws. In some embodiments, a surgeon may push down on each implant receiver 20 simultaneously and in other embodiments a surgeon may push down on each implant receiver 20 in sequence. For example, a surgical instrument may push implant receiver 20 down such that the upper and lower rings 8, 9 are seated around the head portion 11 of bone screw 10 and nested within and retained by corresponding cavities 8a, 9a of base portion 21, for example. In seating upper and lower rings 8, 9 in corresponding cavities 8a, 9a implant receivers 20 may be secured to bone screws 10. Although the discussion and illustrations herein are framed in the context of uniaxial bone screws, it is contemplated that in some embodiments, at least one of the first and second bone screws 10 may be configured as multi-axial screws, sagittal angulation screws, pedicle screws, mono-axial screws, uni-planar screws, fixed screws, anchors, tissue penetrating screws, conventional screws, expanding screws. In some embodiments, bone screws 10 may be employed with wedges, anchors, buttons, clips, snaps, friction fittings, compressive fittings, expanding rivets, staples, nails, adhesives, posts, connectors, fixation plates and/or a post, to name a few possible example configurations. 24

FIG. 8 is a perspective view of a rod for use with disclosed spinal implant systems 100. At least one advantage of rod 45 may be that end caps 46 prevent rod 45 from sliding out of and/or uncoupling from the first and second receivers 20, for example Additionally, by utilizing rod 45, a spinal implant system 100, or at least a portion thereof, may be pre-assembled before commencing a surgery. However, other systems may be pre-assembled and rely on rod 40, rather than rod 45, for example Another advantage of delivering a pre-assembled spinal implant system 100 is that a surgeon may relatively quickly secure the pre-assembled spinal implant system 100 to a pair of adjacent vertebrae of a patient, for example.

Figure 9:
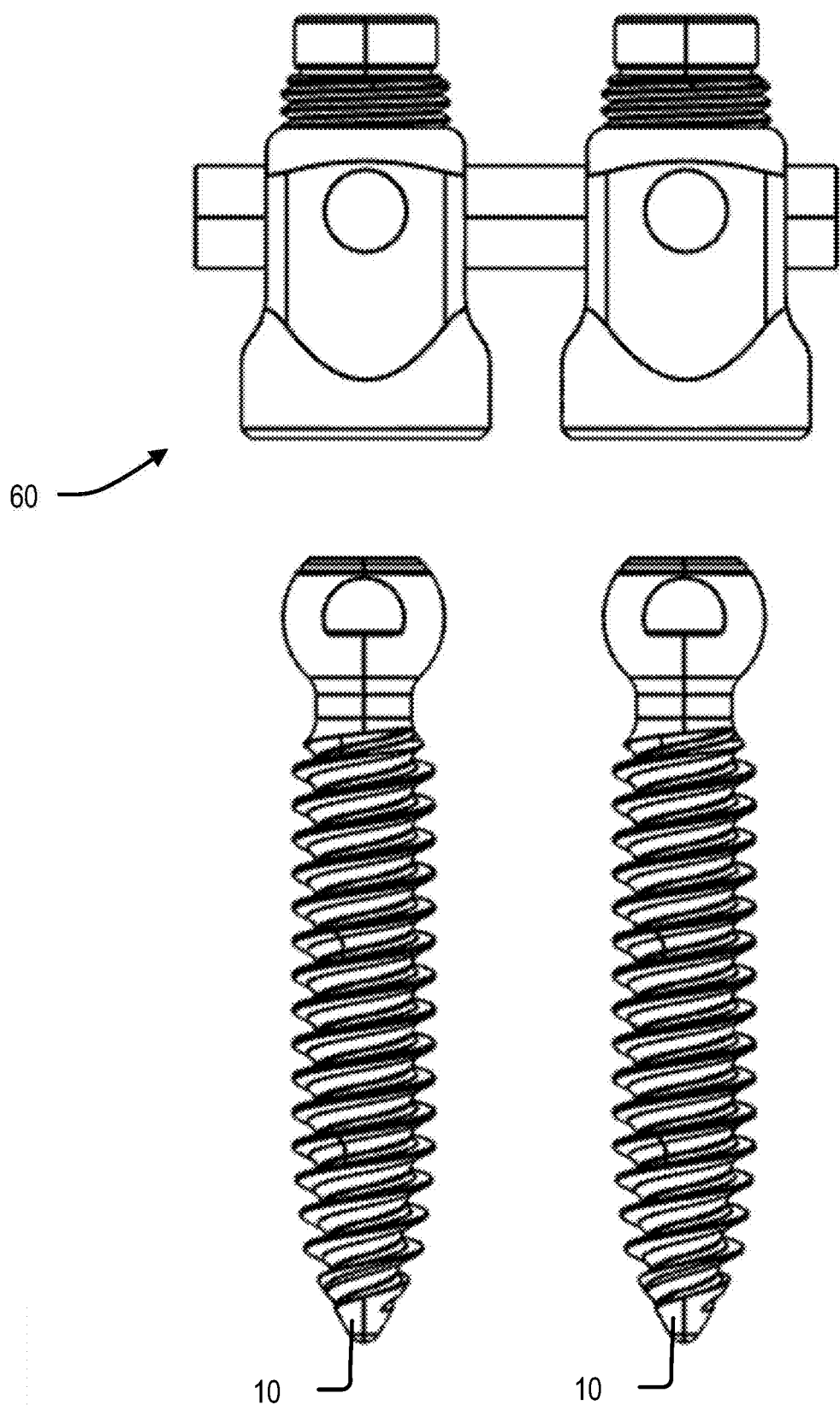
FIG. 9 is side view of a pre-assembled portion of a spinal implant system before being securely coupled to a pair of bone screws.
Figure 10:
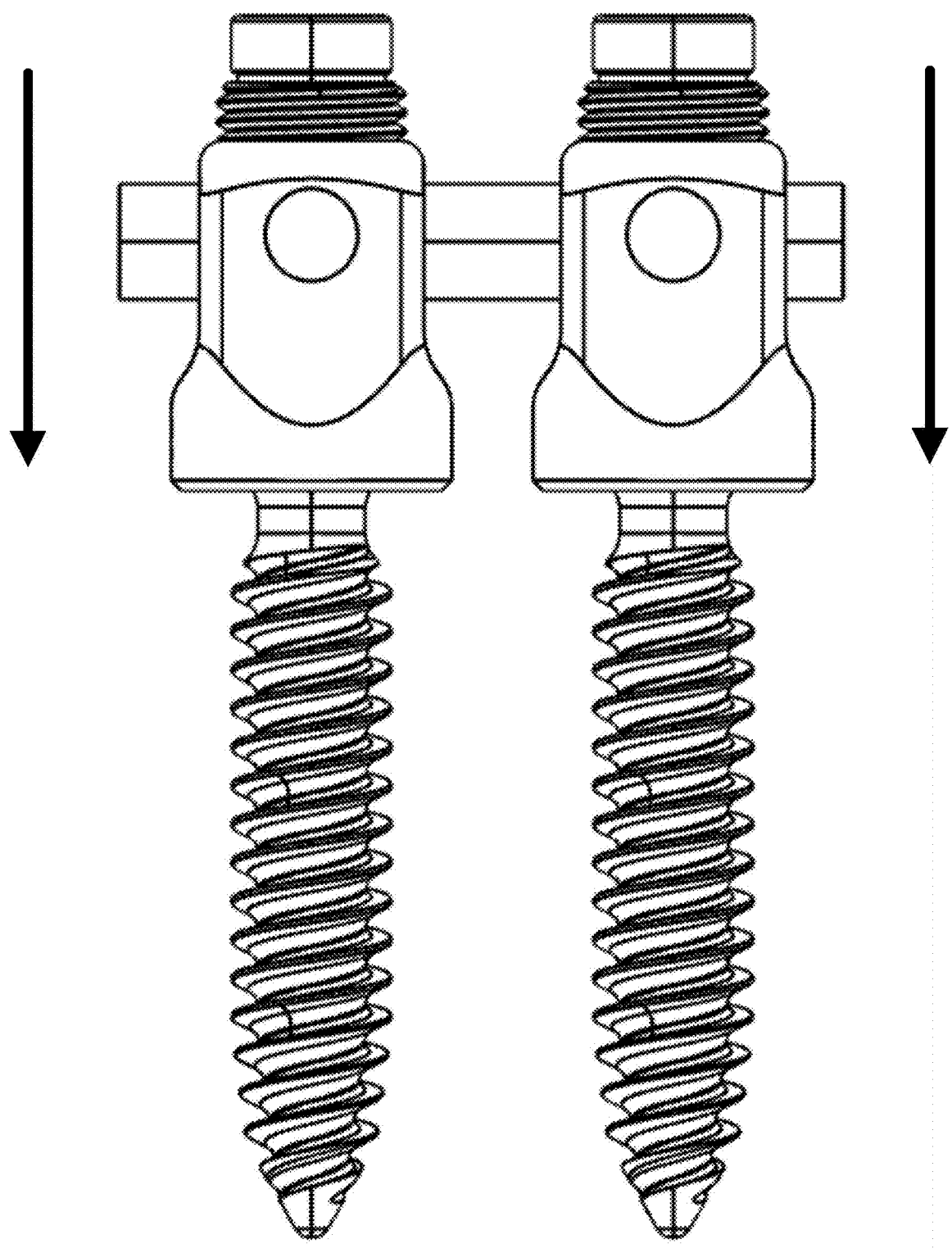
FIG. 10 is side view of the pre-assembled portion of a spinal implant system after being securely coupled to a pair of bone screws.

FIGS. 9 and 10 are side views of a pre-assembled spinal implant 60. As shown in FIG. 9, a rod 40 is secured within the passageways 22 of first and second implant receivers 20, for example. As explained above, rod 40 may be substituted for rod 45 in some embodiments. Rod 40 may be securely retained within passageways 22 due to first and second set screws 50 pushing down against rod 40. For example, first and second set screw 50 may be rotated within threaded passageway 24 such they move downward in the vertical direction and provide a compressive force against rod 40 such that rod 40 is in direct contact with the side portions of passageway 22 and the curved support surfaces 3 of crown 2, for example. In the example embodiment, the upper portion 50 of spinal construct 100 is pre-assembled and the set screws 50 are finger tightened. As shown in FIG. 10, an end user such as a surgeon may push down against the first and second implant receivers 20 such that the head portion 11 of each of the bone screws 10 is securely coupled to the corresponding implant receiver 20, for example.

Figure 11:
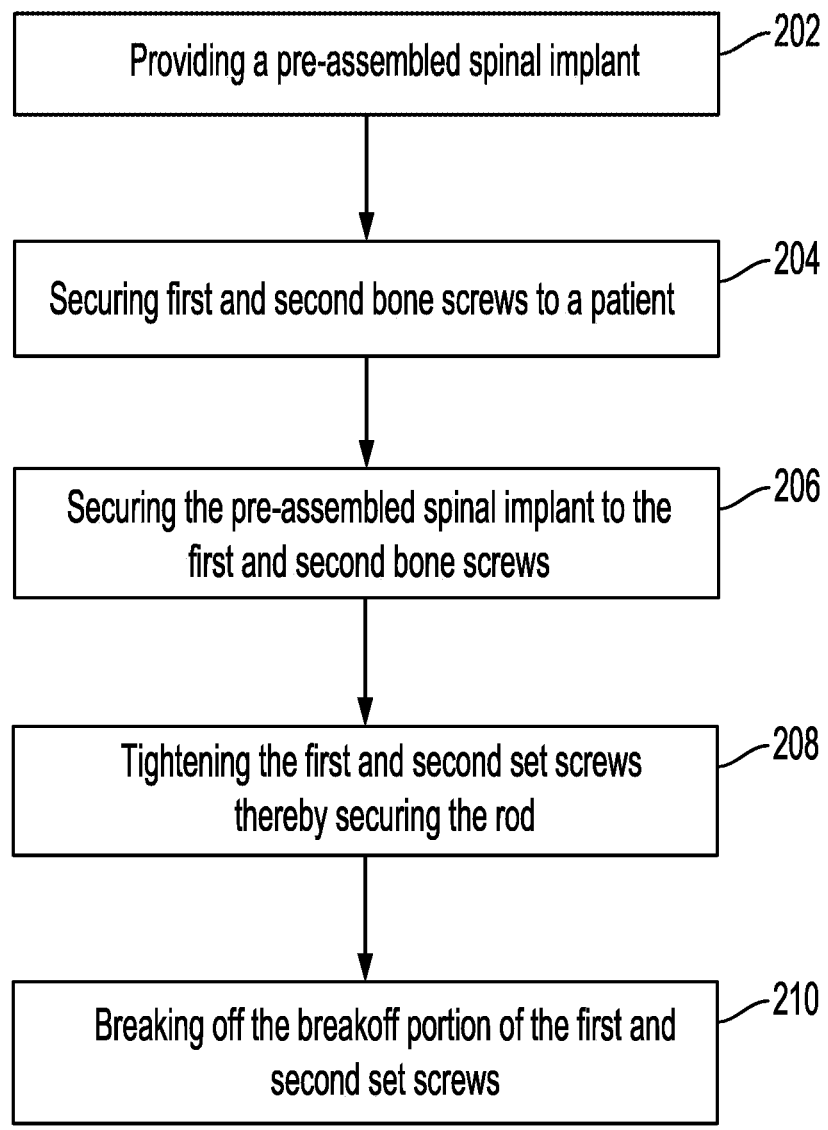
FIG. 11 is a flow chart of an example method of use of disclosed spinal implant embodiments.

FIG. 11 is an example flow chart of a method 200 of installation of a pre-assembled spinal implant 60. The following discussion of method 200 may include reference to components, features, and functionality of spinal implant system 100 as explained above for context, however, the method as disclosed below is not limited to the specific spinal implant system 100 embodiments disclosed above. At step 202, a spinal implant system may be provided, for example an upper portion 50 of spinal implant system 100 or the like. At step 204, a first bone screw 10 or fastener and a second bone screw 10 or fastener may be secured to a patient's anatomy, for example, a pair of bone screws 10 may be secured to adjacent vertebrae of a patient. At step 206, the pre-assembled spinal implant may be secured to the first and second bone screws 10. For example, as shown in FIG. 10, the first and second implant receivers 20 are secured to the first and second bone screws 10 by pushing down on the first and second implant receivers 20. For example still, each implant receiver 20 may be secured to a corresponding bone screw 10 by pushing implant receiver 20 downward and seating various locking rings 8, 9 around the head portion 11 of bone screw 10 and within various receiving cavities 8a, 9a, of implant receiver 20 as explained above. In some embodiments, the first and second implant receivers 20 may be secured to the first and second bone screws simultaneously by, for example, a pair of reduction instruments similar to the rod-reducing instrument described in U.S. Pat. No. 6,790,209, titled Rod Reducer Instruments and Methods, the entire contents of which are incorporated herein in their entirety. At step 208, a rod 40 (or rod 45) may be secured in a final position by sufficiently tightening the first and second set screws 50. For example, the first and second set screws 50 may be rotated by a driver instrument and advanced downward along vertical axis A-A such that they directly contact rod 40 and retain rod 40 in place by a compressive force. At step 210, a breakoff portion of each of the first and second set screws 50 may be broken off, for example breakoff portion 52 may be broken off by a breakoff instrument such as the instruments disclosed in U.S. application Ser. No. 17/104,897, titled Combination Set Screw Breakoff and Tab Breaker Instrument, for example.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An implant, comprising:
   a preassembled combination of a first implant receiver, a second implant receiver, and a rod;
   the first implant receiver having a first rod receiving passageway extending through a first sidewall and through a second sidewall of the first implant receiver in a lateral direction, the first implant receiver having a first threaded passageway extending in a longitudinal direction;
   the second implant receiver having a second rod receiving passageway extending through a third sidewall and through a fourth sidewall of the second implant receiver in the lateral direction, the second implant receiver having a second threaded passageway extending in the longitudinal direction;
   a first set screw having a first outside thread pattern extending along an outside circumferential surface of the first set screw and having a size and shape corresponding to a size and shape of the first threaded passageway; and
   a second set screw having a second outside thread pattern extending along an outside circumferential surface of the second set screw and having a size and shape corresponding to a size and shape of the second threaded passageway,
   wherein the rod of the preassembled combination extends in the lateral direction through the first and second rod receiving passageways, includes a first endcap and a second endcap, and is constrained from moving in the longitudinal direction by the first and second rod receiving passageways.

2. The implant of claim 1, wherein:
   the first implant receiver includes a first base portion for coupling to a first bone screw, and
   the second implant receiver includes a second base portion for coupling to a second bone screw.

3. The implant of claim 2, comprising:
   a first crown having curved surfaces having a size and shape corresponding to an underside of the rod, the first crown being positioned within the first base portion and above the first bone screw; and
   a second crown having curved surfaces having a size and shape corresponding to the underside of the rod, the second crown being positioned within the second base portion and above the first bone screw.

4. The implant of claim 3, wherein at least one of the first base portion and second base portion is configured for mating with a uni-axial bone screw.

5. The implant of claim 4, wherein, in a top down view, the rod extends in the lateral direction such that the rod is oriented directly above the first bone screw and second bone screw.

6. The implant of claim 1, wherein:
   a solid first upper surface of the first implant receiver is disposed above the first rod receiving passageway, and
   a solid second upper surface of the second implant receiver is disposed above the second rod receiving passageway.

7. The implant of claim 1, wherein a perimeter of the first rod receiving passageway is enclosed, and a perimeter of the second rod receiving passageway is enclosed.

8. The implant of claim 1, wherein the preassembled combination comprises at least the first implant receiver, second implant receiver, first set screw, second set screw, and rod such that the first set screw is disposed in the first threaded passageway and the second set screw is disposed in the second threaded passageway.

9. The implant of claim 1, wherein a size of the first endcap is greater than a size of the first rod receiving passageway and a size of the second endcap is greater than a size of the second rod receiving passageway.

10. The implant of claim 1, wherein, in a cross section view, the rod comprises an oval shape.

11. The implant of claim 10, wherein the first and second rod receiving passageways comprise an opening shaped like an oval, respectively.

12. The implant of claim 1, wherein, in a cross section view, the rod comprises a circular shape.

13. The implant of claim 12, wherein the first and second rod receiving passageways comprise an opening shaped like a circle, respectively.

14. The implant of claim 1, wherein the first and second set screws are break off set screws.

15. A method for installing a spinal implant, comprising:
providing a pre-assembled implant, comprising:
a rod extending in a lateral direction;
a first implant receiver having a first rod receiving passageway extending through a first sidewall and through a second sidewall of the first implant receiver in the lateral direction, the first implant receiver having a first threaded passageway extending in a longitudinal direction and a first base portion for coupling to a first bone screw;
a second implant receiver having a second rod receiving passageway extending through a third sidewall and a fourth sidewall of the second implant receiver in the lateral direction, the second implant receiver having a second threaded passageway extending in the longitudinal direction and a second base portion for coupling to a second bone screw;
a first set screw having a first outside thread pattern extending along an outside circumferential surface of the first set screw and having a size and shape corresponding to a size and shape of the first threaded passageway; and
a second set screw having a second outside thread pattern extending along an outside circumferential surface of the second set screw and having a size and shape corresponding to a size and shape of the second threaded passageway,
wherein the rod extends in the lateral direction through the first and second rod receiving passageways and is constrained from moving in the longitudinal direction by the first and second rod receiving passageways;
securing first and second bone screws to a patient; and
securing the pre-assembled spinal implant to the first and second bone screws.

16. The method of claim 15, further comprising tightening the first and second set screws against the rod such that the rod is secured in place relative to the implant.

17. The method of claim 15, wherein securing the pre-assembled spinal implant to the first and second bone screws further comprises orienting the pre-assembled spinal implant such that, in a top down view, the rod is oriented directly above the first bone screw and second bone screw.

18. The method of claim 17, further comprising:
constraining the rod in the longitudinal direction, and
preventing the rod from sliding out of the first rod receiving passageway and second rod receiving passageway.

19. The method of claim 17, wherein the securing the pre-assembled spinal implant to the first and second bone screws step further comprises simultaneously securing the first implant receiver to the first bone screw and the second implant receiver to the second bone screw.

* * * * *